United States Patent
Gupta

(10) Patent No.: US 6,762,035 B1
(45) Date of Patent: Jul. 13, 2004

(54) METHOD AND TEST STRIPS FOR THE MEASUREMENT OF FAT LOSS DURING WEIGHT LOSS PROGRAMS

(76) Inventor: Surendra K. Gupta, 19 Taywood Ct., Laguna Niguel, CA (US) 92677

( * ) Notice: Subject to any disclaimer, the term of this patent is extended or adjusted under 35 U.S.C. 154(b) by 176 days.

(21) Appl. No.: 10/067,660

(22) Filed: Feb. 4, 2002

(51) Int. Cl.$^7$ ............................ C12Q 1/32; C12Q 1/00; C12N 1/00; G01N 33/53
(52) U.S. Cl. ............................ 435/26; 435/4; 435/829; 435/968; 435/970
(58) Field of Search ............................ 435/26, 4, 970

(56) References Cited

U.S. PATENT DOCUMENTS

| | | | |
|---|---|---|---|
| 3,212,855 A | 10/1965 | Mast et al. | 23/253 |
| 4,147,514 A | 4/1979 | Magers et al. | 23/230 |
| 4,348,205 A * | 9/1982 | Lipton et al. | 23/230 |
| 4,440,724 A | 4/1984 | Tabb et al. | 422/56 |
| 5,510,245 A | 4/1996 | Magers | 435/26 |
| 5,618,686 A | 4/1997 | Kojima et al. | 435/26 |
| 5,633,143 A | 5/1997 | Ueda et al. | 435/26 |
| 5,801,059 A | 9/1998 | Smith et al. | 436/128 |
| 5,902,731 A * | 5/1999 | Ouyang et al. | 435/26 |
| 6,200,773 B1 | 3/2001 | Ouyang et al. | 435/26 |
| 6,420,128 B1 * | 7/2002 | Ouyang et al. | 435/14 |

OTHER PUBLICATIONS

Byrne, Hilary et al.; "Evaluation of an. ." Diabetes Care, vol. 23, No. 4, Apr. 2000.

* cited by examiner

*Primary Examiner*—Louise N. Leary

(57) ABSTRACT

A method for monitoring the progress of fat loss in a patient during a weight loss program which comprises, contacting a body fluid sample from said patient with a solid test strip to provide a color indication of the presence in said body fluid of β-hydroxybutyrate, optionally together with acetoacetate and/or acetone.

39 Claims, No Drawings

METHOD AND TEST STRIPS FOR THE MEASUREMENT OF FAT LOSS DURING WEIGHT LOSS PROGRAMS

BACKGROUND OF THE INVENTION

In Weight-Loss Programs, whether initiated as a diet and/or exercise regiment due to obesity or as a treatment in certain diseases such as diabetes, cardiovascular disorders or epilepsy, excess fat in the body is metabolized into smaller chemical units, called ketone bodies, comprised of three components: β-hydroxybutyrate, acetoacetate and acetone.

This invention relates to methods for the measurement of a biochemical marker, ketone bodies i.e. (a) total ketone bodies consisting of all three components i.e. β-hydroxybutyrate, acetoacetate, and acetone. (b) β-hydroxybutyrate in conjunction with acetoacetate or (c) β-hydroxybutyrate alone. The invention particularly relates to its convenient use at home to measure loss of fat during weight-loss programs. The invention includes a disposable, convenient test strip configuration as a solid-phase or dry-chemistry test, which measures Total Ketone bodies, all three components—β-hydroxybutyrate, acetoacetate and acetone. Additionally, the invention relates to a disposable strip which measures β-hydroxybutyrate and acetoacetate in one step, and a strip that measures β-hydroxybutyrate alone which when dipped in urine produces a positive signal, such as a color indicative of fat loss during weight-loss program. The intensity of the color on the strip is an indicator of relative concentration of the analyte(s) present in the sample, thus relates to the relative loss of fat. Such a non-invasive tool can prove to be very useful as a psychological stimulator for a person who needs to lose weight.

There are millions of people who are obese and go on some of type of diet, for example Weight-watcher®, Jenny-Craig, NutriSystem, Atkins diet, The New Beverly Hill Diet, Liquid diet, The Pritlin Principle diet, in order to lose weight. However, the majority of people who go on diets gain back all lost weight within a short period of time. In the U.S. alone, it is estimated that more than 60% of the population is obese. Obesity is the leading cause of many serious diseases such as diabetes, hypercholesterolimea that eventually leads to kidney and liver failure.

Just mere weight loss measurement on a weighing scale during dieting is not sufficient as overweight people must lose fat during dieting, not protein. Therefore, it will be of great social and medical benefit if a biochemical marker is invented which when used on a daily basis can indicate to a person whether indeed fat loss is taking place or not while one is dieting. Such a psychological tool can considerably enhance the efforts of a person in losing weight as well as maintaining his or her ideal weight.

It has been known that when body fat, i.e. fatty acid, is degraded, which is the principal component of body fat, it breakdowns ultimately into small molecules in the form of ketone bodies. Ketone bodies consist of a group of three chemicals: β-hydroxybutyrate, acetoacetate, and acetone. β-hydroxybutyrate is a major ketone body comprised of about 75–80% of total ketone bodies, acetoacetate comprised of about 20–25% of total ketone bodies and acetone which is present only in trace quantities less than 2%). Because of acetone's low concentration and its instability, it is seldom measured by itself. Instead, acetoacetate and acetone are measured by a nitroprusside reaction in alkaline conditions. Several patents describe methods and devices for measurement of acetoacetate using nitroprusside reaction, such as U.S. Pat. No. 3,212,855 to Mast; U.S. Pat. No. 4,147,514 to Magers and Tabb; U.S. Pat. No. 4,440,724 to Tabb and Burrows. Acetoacetate test strips have been commercially available for many years (Bayer diagnostics, Roche diagnostics), which measure acetoacetate and acetone in urine. They produce purple color and the intensity of the color approximates the concentration of acetoacetate present in urine or serum. These strips are generally used by a patient who has diabetes (especially Type I diabetic patients). These strips are erroneously referred as to "Test for Ketone or Ketone body", even though they only measure the minor component of ketone bodies i.e. acetoacetate and acetate which comprise less than 20–25% of total ketone bodies and these strips do not measure the major component, that is, β-hydroxybutyrate at all. Even though, these strips are insensitive to β-hydroxybutyrate, such strips have been successfully used in some diet programs such as the Atkins' diet that is comprised of high fat and very low carbohydrates.

Similarly, U.S. Pat. No. 5,260,219 to Fritz teaches the use of test strips in the measurement of acetoacetate in diet programs. Surprisingly, it has been found by the present invention that these strips measuring acetoacetate/acetone are mostly insensitive when dipped in the urine of those individuals who are on 1000–1500 calories/day of "balanced" diets, unlike the Atkins' diet which is high in fat and very low in carbohydrates content, and therefore are not useful as biochemical markers for general or common utilization in weight loss programs. In contrast, the present invention is based on the discovery that strips, which measure (a) β-hydroxybutyrate alone (which is about 3 to 4 time more in concentration than acetoacetate) or (b) both β-hydroxybutyrate and acetoacetate or (c) total ketone bodies, that is, all three components are very sensitive and can measure even very small amount of these chemicals in urine and other biological fluids. Such sensitive strips can successfully be used during any weight loss program and color produced is reflective of the presence of these chemicals in the fluid.

SUMMARY OF THE INVENTION

It is, therefore, an object of the present invention to a provide convenient and sensitive solid-phase methods for measurement of (a) total ketone bodies, that is all three components, β-hydroxybutyrate, acetoacetate and acetone; (b) β-hydroxybutyrate and acetoacetate in one step; and (c) β-hydroxybutyrate alone in biological samples, by means of a non-invasive sample, such as urine, which produces color that can be used for detecting the breakdown of fat (or fatty acids) in persons who are on weight-loss programs.

It is also an objective of the present invention to provide a convenient, and sensitive solid-phase or dry chemistry device that can be used for measurement of (a) Total Ketone bodies that is all three components, β-hydroxybutyrate, acetoacetate and acetone; (b) β-hydroxybutyrate and acetoacetate in one step; and (c) β-hydroxybutyrate alone in biological samples, with non-invasive samples, such as urine which produce color that can be used for detecting the breakdown of fat (or fatty acids) in persons who are on weight-loss programs.

It is also an objective of this invention to provide strips for detection of breakdown of fat (or fatty acid) in persons who are on Weight-Loss programs and are on low calories diet 1000–1500 or less per day. These strips show positive color when dipped in morning urine whereas the commercially available strips for ketone, which only measures acetoacetate and acetone, are insensitive. Thus, the invention provides for the first time a biochemical marker as a psychological stimulator to a person who is on weight loss programs.

A method for monitoring the progress of fat loss in a patient during a weight loss program which comprises, contacting a body fluid sample from said patient with a solid test strip to provide a color indication of the presence in said body fluid of β-hydroxybutyrate, optionally together with acetoacetate and/or acetone.

A method of assaying for β-hydroxybutyrate and acetoacetate in a sample which comprises:
  a) contacting a sample with a composition comprised of β-hydroxybutyrate dehydrogenase (β-HBD) and nicotinamide adenine dinucleotide (NAD) at a pH of less than 8.5, whereby
    (i) β-hydroxybutyrate (β-HB) reacts with NAD to produce acetoacetate and reduced-type nicotinamide adenine dinucleotide (NADH),
    (ii) a portion of the NADH produced in (i) reacts with acetoacetate in the presence of β-HBD to produce β-HB, and
    (iii) a portion of the NADH produced in (i) is converted into a colored product,; and
detecting the presence of said colored product.

A test strip for assaying for β-hydroxybutyrate, acetoacetate, and acetone in a sample comprising:
  a) a support layer; and
  b) a reagent layer on said support layer, said reagent layer comprising:
    i) β-hydroxybutyrate dehydrogenase (β-HBD),
    ii) nicotinamide adenine dinucleotide (NAD),
    iii) a tetrazolium dye precursor, and
an electron mediator.

DETAILED DESCRIPTION OF THE INVENTION

For the use in weight-loss programs, sensitive, convenient methods are presented here, specifically a method which (a) simultaneously measures total ketone bodies, i.e., all three components—β-hydroxybutyrate, acetoacetate and acetone; (b) simultaneously measures β-hydroxybutyrate and acetoacetate, and (c) measures only the major Ketone body, that is, β-hydroxybutyrate in biological fluids including urine, blood/serum, saliva. In addition, solid-phase devices such as a test strip are described in the present invention as a means for (a) simultaneous measurement of Total Ketone bodies, that is all three components—β-hydroxybutyrate, acetoacetate and acetone; (b) measurement of β-hydroxybutyrate and acetoacetate; and (c) measurement of only β-hydroxybutyrate. These test strips can be used frequently as a non-invasive tool and a biochemical marker to ensure that indeed fat is being metabolized during various diet programs. Each of these strips is extremely sensitive, that is, when dipped in urine frequently or every morning will show a positive color, if any amount of fat is being metabolized during the day, thus serving as a psychological stimulator and tool to a person involved in any weight-loss program.

There is no dry-chemistry method or solid phase device known to measure Total Ketone bodies (TKB). The present invention, for the first time provides a novel, convenient method and an impregnated test strip in a solid-phase and dry-chemistry format for measurement of TKB that can be used at the patient's site, especially in a weight-loss program. The method and device use β-hydroxybutyrate dehydrogenase to convert β-hydroxybutyrate to acetoacetate and simultaneously acetoacetate produced by said reaction, endogenous acetoacetate and acetone are measured by known colorimetric methods.

A process for measuring TKB was described for use in an automated analyzer, without employing an impregnated test strip, in U.S. Pat. No. 5,801,059 to Smith et al. However, as this method required an expensive automated analyzer and professional personnel to perform the test, it is not suitable and cannot be used by a patient at home.

U.S. Pat. No. 5,618,686 to Kojima et al describes a method for measurement of β-hydroxybutyrate and acetoacetate, which is referred mistakenly as Total Ketone bodies (TKB). The method is a two-step process. In the first step, acetoacetate is converted in β-hydroxybutyrate in the sample with the aid of β-hydroxybutyrate dehydrogenase (HBD) and NADH (reduced nicotoniamide adnenine dinucleotide) and in the second step measures both sources of β-hydroxybutyrate, originally existed in the sample and β-hydroxybutyrate converted by the first step from acetoacetate with the aid of β-hydroxybutyrate dehydrogenase and NAD. However, this method suffers from (a) it can only be used with an automated analyzer and both steps cannot be combined due to difference in pH requirements for these steps so it cannot work as a one-step convenient method and (b) it measures NADH at 340 nm wavelength and does not produce color.

Similarly, another method to measure β-hydroxybutyrate and acetoacetate is described in U.S. Pat. No. 5,633,143 to Ueda et al, which is again a two steps process. In this case also, in the first step acetoacetate is first converted to β-hydroxybutyrate and then β-hydroxybutyrate is measured using β-hydroxybutyrate dehydrogenase and a thiol derivative of NAD (thionicotinamide adenine dinnucleotide), which can be measured at 400 nm wavelength. Although the method is sensitive, it suffers from the detriments that (a) NADH and thio-NAD are not compitable and cannot be mixed together as one reagent in one-step method or device and (b) thio-NAD is difficult to function as a coenzyme of β-hydroxybutyrate dehydrogenase as it is not a natural coenzyme and has a very high Km, an unusually high concentration of β-hydroxybutyrate dehydrogenase is required and hence becoming uneconomical, and (c) a yellow color produced at 400 nm is difficult to recognize visually and prone to interference from hemolysis and presence of bilirubin.

The above two-step method can be used in liquid assays and can be adapted to large clinical analyzers even though it requires two separate steps, however, it cannot be employed to develop a convenient solid-phase device or dry-chemistry method or device, which requires one-step process.

In the present invention, it was very surprisingly found, that if the reaction 1A which converts β-hydroxybutyrate in presence of NAD (nictonimaide adenine dinucleotide) to acetoacetate and NADH (reduced NAD), as described below, is carried out at pH less than 8.5, for example pH 8.0, or 7.75 or 7.5, the reaction 1B, that is conversion of NADH with tetrazolium salts in presence of diaphorase, becomes slower than the reaction 1A. As a result, part of NADH, which was not converted to color by diaphorase and tetrazolium salt, becomes available to be used in the following reaction (2) to measure acetoacetate that is also present in the sample as shown here.

Reaction 1:

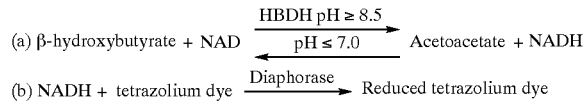

(b) NADH + tetrazolium dye →(Diaphorase)→ Reduced tetrazolium dye

Reaction 2:

By this method, the test not only measures β-hydroxybutyrate in the sample, it was also measuring acetoacetate simultaneously present in the sample (i.e. endogenoss in a one step process. Moreover, in the present reaction scheme, it becomes a cyclic reaction between reaction 1 and 2 and thus continue to produce color over time thus increasing sensitivity several fold.

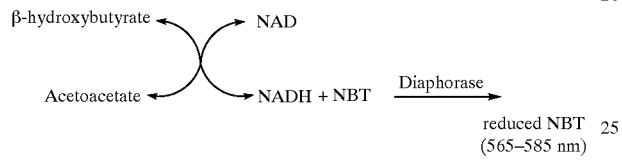

This "cyclic" methodology, unexpectedly, leads to a very sensitive method to measure both β-hydroxybutyrate and acetoacetate in the sample as it continually produces color over time. Additionally, the method produces purple color and shades of purple color, which reflects the relative concentration of β-hydroxybutyrate and acetoacetate in a sample, which can easily be visually differentiated. It is also possible to measure NADH by other known methods, such as electrochemical sensors, but methods producing visual color are easily adopted by patients at home.

Although, methods of measuring β-hydroxybutyrate in biological fluids using the enzyme β-hydroxybutyrate dehydrogenase (HBD) in the presence of NAD which produces NADH that is measured in the UV region at 340 nm wavelength, (Ref: Williamson et al, 1962, "Enzymatic Determination of D(-)-beta-Hydroxybutyric Acid and Acetoacetate acid in Blood", Biochem. J., 82:90–96) have been known for a long time, there was no easy calorimetric method known to measure β-hydroxybutyrate. (Ref: Harano et al.,1984, "Development of Paper-Strip Test for 3-hydroxybutyrate and its Clinical Application", Diabetic Care, 7, p. 481–485; Harano et al., 1990, "Development of Stable Film Test for Rapid Estimation of Blood or Plasma 3-hydroxybutyrate," Diabetic care, 13: 522–524; and a KetoSite® test available from GDS Technology, Inc, Elkhart, Ind. 46514 dated Dec. 19, 1993 product insert. (See, Tietz Text book of Clinical Chemistry, 3rd edition, edited by Burtis and Ashwood,1999, p786–787). In these methods, β-hydroxybutyrate dehydrogenase and NAD are used to react with β-hydroxybutyrate and the reaction produces NADH which is measured by the reaction with tetrazolium salt (such as NBT i.e. nitrobluetetrazolium) in presence of excess of diaphorase enzyme thus producing color which is proportionate to its concentration in blood. In these systems, it is necessary to have pH of the reaction higher than 8.5 to derive the reaction from left to the right, and to have pH of 7.0 or less to derive the reaction from right to the left as shown in the following diagram:

Reaction 1:

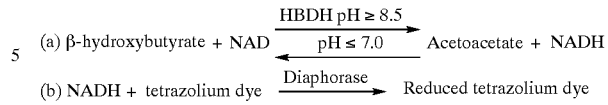

(b) NADH + tetrazolium dye →(Diaphorase)→ Reduced tetrazolium dye

These tests have been used for patients who produce β-hydroxybutyrate in blood during severe ketoacidosis caused by serious insulin deficiencies in patients with diabetes. Surprisingly, the present inventor has discovered that the β-hydroxybutyrate strip or card can also be used by persons using blood as a sample who are on low calories diet. The intensity of the color produced is reflective of level of β-hydroxybutyrate in blood. However, the use of blood, as an invasive method, is not practical for use by a common person who is on a low calorie diet. The strip for β-hydroxybutyrate will obviously be more useful if it can be used for urine testing, as opposed to blood, since a urine sample is non-invasive and can be tested conveniently by anyone at anytime. It is also possible to use other non-invasive fluids such as saliva or sweat as done for alcohol measurement. However, it was surprisingly discovered by the present inventor that such test cards, commercially available by GDS Technology, Inc, for β-hydroxybutyrate cannot be used for urine for two reasons (a) the reaction is conducted at pH higher than 8.5 and other components such as sulfahydryl drugs in urine (also in blood) which can reduce tetrazolium salt itself thus provide false positive results and (b) the enzyme β-hydroxybutyrate dehydrogenase (HBD) generally used in the strip is inhibited by chloride salt which is abundantly present in urine, and thus the strip is not able to measure β-hydroxybutyrate in urine, which will be a sample of choice. In the present invention it has surprisingly been found that it is possible to overcome these problems and develop a strip for testing β-hydroxybutyrate in urine by either using a high amount of β-hydroxybutyrate dehydrogenase (e.g, 10 to 20 the times amount than generally is required) or by using β-hydroxybutyrate dehydrogenase, which is not inhibited by chloride ions. The interferences from other substances such as sulfahydryl drugs present in urine have been able to overcome by running the reaction at pH of 8.5 or less.

The strips developed for measurement of β-hydroxybutyrate, which is generally present at an amount 34 times greater than acetoacetate, by this invention can, therefore, be successfully used in testing urine of persons who are on low calories diet or patients suffering from diabetes. The test strip of the invention for β-hydroxybutyrate is, therefore, significantly more sensitive to measure than the test strip commercially available for ketone measurement which only measures the minor components of acetoacetate and acetone.

There are alternative colorimetric methods to measure β-hydroxybutyrate that use Ellman's reagent, β-hydroxybutyrate dehydrogenase, lipomide dehydrogenase, D,L-Lipomide and NAD incorporated into a carrier matrix for measurement of β-hydroxybutyrate (U.S. Pat. No. 5,190,863 to Magers, U.S. Pat. No. 5,326,697 to Magers, U.S. Pat. No. 5,510,245 to Magers. These methods require a complex system, not cost-effective for general use and do not demonstrate potential for use in weight loss programs. The signal produced in these methods is generally a color. An electrochemical sensor measuring NADH as change in current is commercially available by Abbott (Medisense), Abbott Park, Chicago, Ill. for the use in ketoacidosis in diabetes. An attempt was recently made to use this device in a weight-loss program using whole blood (Byrne et al, 2000, Diabetes care, 23, 500–503). However, as such devices do not produce color and are instrument based, they are not convenient for home use, especially for weight loss program. Additionally as described earlier, an non-invasive sample will be a preferred sample, and above electrochemical device did not function when urine was used as sample.

Thus, apart from the present invention, there is no sensitive, easy to use solid-phase device measuring color known that can be used as a tool for measurement of fat loss during weight loss program. Surprisingly, it was found that the strips according to the present inventor—i.e. a strip measuring TKB, a strip measuring β-hydroxybutyrate and acetoacetate and a strip measuring β-hydroxybutyrate alone, were extremely sensitive and showed positive color. They were able to measure trace or small amount of ketone bodies during fat metabolism when dipped in everyday urine whereas commercially available strip measuring acetoacetate were negative when person was 1000–1500 calories balanced diet.

EXAMPLE 1

A Method and Strip Device to Measure Total Ketone Bodies, that is, all Three Ccomponents: β-hydroxybutyrate, Acetoacetate and Acetone as one Step.

As an example, the formulation contains β-hydroxybutyrate dehydrogenase enzyme (HBD) and NAD with converts β-hydroxybutyrate to acetoacetate at pH 8.0 and then "converted acetoacetate" and endogenous acetoacetate and acetone is measured by nitroprusside reaction:

| β-hydroxybutyrate + NAD | HBDH | Acetoacetate + NADH |
|---|---|---|
| Acetoacetate color (Converted + Endogenous) | + acetone | Nitoprusside at pH 8.5 Purple |

The formulation contains:

| Tris-Buffer, pH 8.0 | 1M |
|---|---|
| β-hydroxybutyrate dehydrogenase | 100 U/mL |
| NAD | 3% |
| Sodium Nitroprusside | 5% |
| Magnesium sulfate heptahydrate | 30% |

The filter paper such as Whatman-54 is dipped in the above formulation is dried in oven at 45° C. for 20 minutes. The strips are made by sticking a ¼" of layer of said paper on the bottom of the polystyrene card which is 12" long and 3" high with the help of double adhesive tape. The card is cut lengthwise into 48 strips of ¼"×3" high strips. The strips, which measure Total Ketone bodies, are used for testing of biological fluids. These strips are referred to as "TKB". The use of TKB in weight loss program is demonstrated in Example 6.

Instead of nitroprusside, acetoacetate can also be measured by known diazonium salt, which produces color at 645 nm wavelength.

EXAMPLE 2

A Method and Device to Measure β-hydroxybutyrate and Acetoacetate Simultaneously in a "Cyclic" Fashion.

The formulation contains β-hydroxybutyrate dehydrogenase, NAD, NBT and diaphorase at pH 8.0.

| Tris-HCl, pH 8.0 | 0.1M |
|---|---|
| β-hydroxybutyrate dehydrogenase | 200 U/mL |
| NAD | 3% |
| NBT | 0.2% |
| Diaphorase | 10 U/mL |
| Magnesium chloride 0.1% | |
| Surfonyl | 0.06% |

The filter paper such as Whatman-54 is dipped in the above formulation is dried in oven at 45° C. for 20 minutes. The strips are made by sticking a ¼" of layer of said paper on the bottom of the polystyrene card which is 12" long and 3" high with the help of double adhesive tape. The card is cut lengthwise into 48 strips of ¼"×3" high strips. The strips are used for testing of biological fluids. These strips, which measure β-hydroxybutyrate and acetoacetate both are referred as "HB&AA", and its use in weight loss program is demonstrated in Example 6.

EXAMPLE 3

A Method and Device to Measure β-hydroxybutyrate Alone in Serum (Blood) in Samples Obtained from Weight Loss Program that uses Normal Concentration of HBD, Similar to the Device Available Commercially as KetoSite® by GDS Technology, Inc.

The formulation contains normal level of β-hydroxybutyrate dehydrogenase (2–5 U/mL), NAD, NBT and diaphorase at pH 8.6

| β- hydroxybutyrate dehydrogenase (Pseudomonas) | 15 U/mL -.2 U per strip |
|---|---|
| NAD | 3% |
| NBT | 0.2% |
| Diaphorase | 30 U/mL |
| Magnesium chloride | 0.1% |
| Surfonyl | 0.05% |
| Tris-HCl, pH 8.6 | 0.1M |

The filter paper such as Whatman-54 is dipped in the above formulation is dried in oven at 45° C. for 20 minutes. The strips are made by sticking a ¼" of layer of said paper on the bottom of the polystyrene card which is 12" long and 3" high with the help of double adhesive tape. The card is cut lengthwise into 48 strips of ¼"×3" high strips. The strips are used for testing of biological fluids. These strips measuring β-hydroxybutyrate alone with "normal" conc. of β-hydroxybutyrate dehydrogenase are referred to as "HB-L".

As demonstrated in Table 1, we surprisingly found that both HB-L strips and KetoSite can be used to measure β-hydroxybutyrate in serum (blood) as one minute test from samples obtained from people on weight-loss program. The relative intensity of purple color is indicated as "+" signs and absence of color is indicated by "−" signs.

TABLE 1

| Serum Samples with β-hydroxybutyrate | HB-L Strips | KetoSite |
|---|---|---|
| 1. 0.12 mM conc. | + | + |
| 2. 0.25 mM conc. | ++ | ++ |
| 3. 0.52 mM conc. | +++ | +++ |
| 4. 1.14 mM conc. | ++++ | ++++ |
| 5. 2.5 mM conc. | ++++++ | ++++++ |

In contrast to serum samples as shown in Table 1, urine containing similar concentration of β-hydroxybutyrate either did not show any color (after one minute) or very light color at higher concentration of β-hydroxybutyrate (Table 2), when dipped in urine. The relative intensity of purple color is indicated as "+" signs and absence of color is indicated by "−" signs.

TABLE 2

| Urine samples with β-hydroxybutyrate | HB-L strip | KetoSite |
|---|---|---|
| 1. 0.11 mM | − (Negative) | − (Negative) |
| 2. 0.22 mM | − | − |
| 3. 0.48 mM | − | − |
| 4. 1.12 mM | − | − |
| 5. 2.22 mM | ++ | + |

EXAMPLE 4

A Method and Device of Measuring β-hydroxybutyrate Alone in Urine: A Strip was Made using High Level of β-hydroxybutyrate Dehydrogenase (200 U/mL) and other Components in the Formulation Similar to Shown in Example 3.

| β-hydroxybutyrate dehydrogenase (Pseudomonas) | 200 U/mL |
|---|---|
| NAD | 3% |
| NBT | 0.2% |
| Diaphorase | 30 U/mL |
| Magnesium chloride | 0.1% |
| Surfonyl | 0.05% |
| Tris-HCl, pH 8.6 | 0.1M |

The filter paper such as Whatman-54 is dipped in the above formulation is dried in oven at 45° C. for 20 minutes. The strips are made by sticking a ¼" of layer of said paper on the bottom of the polystyrene card which is 12" long and 3" high with the help of double adhesive tape. The card is cut lengthwise into 48 strips of ¼"×3" high strips. The strips are used for testing of biological fluids. These strips with high conc. of β-hydroxybutyrate dehydrogenase (i.e. 1 unit or more per strip where 1 unit is the amount whereby 1 U/ml of substrate is oxidized at the pH 8.5 at 30° C. per minute) measuring β-hydroxybutyrate alone are referred to as "HB-H". As shown in Table 3, using "HB-H" strip, it was possible to overcome the detection in sensitivity of urine sample as described in Table 2. Further, the use of HB-H strip in weight loss program is demonstrated in Example 6.

TABLE 3

| Urine samples with β-hydroxybutyrate | HB-H Strip | HB-L strip | KetoSite |
|---|---|---|---|
| 1. 0.11 mM | + | − (Negative) | − (Negative) |
| 2. 0.22 mM | ++ | − | − |
| 3. 0.48 mM | +++ | − | − |
| 4. 1.12 mM | ++++ | − | − |
| 5. 2.22 mM | +++++ | + | + |

EXAMPLE 5

A Method of Measuring B-hydroxybutyrate in Urine using β-hydroxybutyrate Dehydrogenase Enzyme (Alcaligenes) which is not Inhibited by Chloride Ions.

| β-hydroxybutyrate dehydrogenase (from Alcaligenes) | 15 U/mL |
|---|---|
| NAD | 3% |
| NBT | 0.2% |
| Diaphorase | 30 U/mL |
| Magnesium chloride | 0.1% |
| Surfonyl | 0.05% |
| Tris-HCL, pH 8.6 | 0.1M |

The filter paper such as Whatman-54 is dipped in the above formulation is dried in oven at 45° C. for 20 minutes. The strips are made by sticking a ¼" of layer of said paper on the bottom of the polystyrene card which is 12" long and 3" high with the help of double adhesive tape. The card is cut lengthwise into 48 strips of ¼"×3" high strips. The strips are used for testing of biological fluids. These strips using β-hydroxybutyrate dehydrogenase that is insensitive to chloride ions are referred to as "HB-L-A". HB-L-A strips containing "normal" concentration of β-hydroxybutyrate dehydrogenase were able to detect β-hydroxybutyrate in urine, similar to HB-H strip and in contrast to HB-L strip or KetoSite strip (Table 4). The color was measured one minute after dipping in the urine.

TABLE 4

| Urine samples with β-hydroxybutyrate | HB-L-A strip | HB-H Strip | HB-L strip | KetoSite |
|---|---|---|---|---|
| 1. 0.11 mM | + | + | − (Negative) | − (Negative) |
| 2. 0.22 mM | ++ | ++ | − | − |
| 3. 0.48 mM | +++ | +++ | − | − |
| 4. 1.12 mM | ++++ | ++++ | − | − |
| 5. 0.48 mM | +++++ | +++++ | + | + |

EXAMPLE 6

Utility of Strips in Weight Loss Program

The strips TKB (described on Example 1) measuring Total Ketone bodies, HB& AA (described in Example 2) measuring both β-hydroxybutyrate and acetoacetate in one step in a cyclic method, HB-H (as described in Example 4) measuring β-hydroxybutyrate alone, and acetoacetate (AA) commercially available strips for measurement, KetoStix® from Bayer Diagnostics, Elkhart, Ind. were used in weight loss program. These strips were used for twenty days in each morning samples from persons who were on various 1000–1500 calories diets. These strips were dipped in urine and color was visually measured in a semi-quantitatively fashion after one minute. Diet 1 contained approximately 30% carbohydrates, 40% fat, and 30% protein and results are shown in Table 5. Diet 2 contained approximately 40% carbohydrate, 30% fat and 30% protein and results are shown in Table 6. Diet 3 contained approximately 50% carbohydrates, 20–25% fat, and 20–25% protein and results are shown in Table 7. Diet 4, similar to Atkin's diet, was low in carbohydrate and high on fat containing approximately 10% carbohydrates, 40–50% fat, 30–40% protein and results are shown in Table 8. As demonstrated in Table 5, 6, 7, and 8 all three strips (TKB, HB&AA, HB-H) showed a positive color with low level of ketone bodies whereas commercially known strips, which measures only acetoacetate and acetone (AA) that were negative with the exception of Diet 4. All three strips showed a higher intensity of color as compared to AA strip with high fat, low carbohydrates (Table 8).

TABLE 5 with Diet 1

| Sample | TKB Strip | HH&AA Strip | HB-H Strip | AA Strip |
|---|---|---|---|---|
| 1 | + | + | + | − |
| 2 | + | ++ | + | − |
| 3 | ++ | +++ | + | − |
| 4 | ++ | +++ | ++ | + |
| 5 | ++ | ++ | + | − |
| 6 | ++ | ++ | + | − |
| 7 | ++ | + | + | − |
| 8 | ++ | ++ | + | − |
| 9 | + | ++ | + | − |
| 10 | ++ | +++ | − | + |
| 11 | + | + | + | − |
| 12 | ++ | ++ | + | − |
| 13 | + | + | + | − |
| 14 | + | ++ | + | − |
| 15 | ++ | + | + | − |
| 16 | ++ | + | + | − |
| 17 | ++ | ++ | + | − |
| 18 | + | + | − | − |
| 19 | ++ | ++ | + | − |
| 20 | + | + | − | − |

TABLE 6 with Diet 2

| Sample | TKB Strip | HH&AA Strip | HB-H Strip | AA Strip |
|---|---|---|---|---|
| 1 | + | + | + | − |
| 2 | + | ++ | ++ | − |
| 3 | ++ | +++ | ++ | − |
| 4 | ++ | +++ | ++ | − |
| 5 | ++ | ++ | ++ | − |
| 6 | ++ | ++ | ++ | − |
| 7 | ++ | + | + | − |
| 8 | ++ | ++ | + | − |
| 9 | + | ++ | + | + |
| 10 | ++ | +++ | + | − |
| 11 | + | + | − | − |
| 12 | ++ | ++ | + | − |
| 13 | + | + | + | − |
| 14 | + | ++ | + | − |
| 15 | + | + | + | − |
| 16 | + | + | + | − |
| 17 | + | ++ | + | − |
| 18 | + | + | − | − |
| 19 | + | ++ | + | − |
| 20 | + | + | + | − |

TABLE 7 with Diet 3

| Sample | TKB Strip | HH&AA Strip | HB-H Strip | AA Strip |
|---|---|---|---|---|
| 1 | + | + | − | − |
| 2 | + | + | − | − |
| 3 | ++ | ++ | + | − |
| 4 | + | ++ | + | − |
| 5 | ++ | ++ | + | − |
| 6 | + | ++ | + | − |
| 7 | ++ | + | + | − |
| 8 | ++ | ++ | + | − |
| 9 | + | ++ | + | + |
| 10 | + | + | + | − |
| 11 | + | + | + | − |

TABLE 7-continued with Diet 3

| Sample | TKB Strip | HH&AA Strip | HB-H Strip | AA Strip |
|---|---|---|---|---|
| 12 | ++ | ++ | + | − |
| 13 | + | ++ | + | − |
| 14 | + | ++ | + | − |
| 15 | ++ | + | + | − |
| 16 | ++ | + | + | − |
| 17 | ++ | ++ | + | − |
| 18 | + | + | − | − |
| 19 | ++ | ++ | + | − |
| 20 | + | + | − | − |

TABLE 8 with Diet 4

| Sample | TKB Strip | HH&AA Strip | HB-H Strip | AA Strip |
|---|---|---|---|---|
| 1 | + | + | + | − |
| 2 | +++ | +++ | ++ | + |
| 3 | +++ | +++ | ++ | + |
| 4 | ++++ | ++++ | +++ | ++ |
| 5 | ++++ | ++++ | ++ | ++ |
| 6 | ++ | ++ | ++ | + |
| 7 | +++ | +++ | + | ++ |
| 8 | +++ | +++ | ++ | + |
| 9 | ++ | ++ | + | + |
| 10 | ++ | ++ | + | + |
| 11 | ++ | ++ | + | − |
| 12 | ++ | ++ | − | − |
| 13 | + | ++ | + | + |
| 14 | + | ++ | + | + |
| 15 | ++ | ++ | + | − |
| 16 | ++ | ++ | + | + |
| 17 | ++ | ++ | + | − |
| 18 | ++ | ++ | + | − |
| 19 | ++ | ++ | + | − |
| 20 | ++ | ++ | + | − |

Obviously, many modifications and variation of the invention as hereinbefore set forth can be made without departing from the spirit and scope thereof and therefore only such limitations should be imposed as are indicated by the appended claims.

All of the publications referred to herein are hereby incorporated by reference.

What is claimed is:

1. A solid test strip designed for use in monitoring weight loss programs and capable of enabling a person to self-monitor weight loss on a daily basis in a sample of urine, saliva or other bodily fluid that is noninvasively obtainable, which provides a color signal, indicative of the β-hydroxybutyrate content of the sample upon being dipped in the sample, removed, allowed to rest briefly and read, which solid test strip comprises 1) an inert support layer and
2) a dried reagent layer comprising a porous material impregnated with
   a) β-hydroxybutyrate dehydrogenase enzyme ("β-HBD), which is either
      (I) obtained from Alcaligenes or another source such that it is uninhibited by chloride ions or
      (ii) is obtained from a source that is inhibited by chloride ions and is present in a concentration at least 10 to 20 times that used when the β-HBD is obtained from a source such that it is uninhibited by chloride ions, b) nicotinamide dinucleotide ("NAD"),
c) a tetrazolium dye precursor
d) an electron mediator capable of transferring an electron to said dye precursor to effect a color change, and
e) a sufficient amount of a buffer having a pH in excess of 8.5 to maintain the reaction pH above 8.5 when the strip is saturated with urine or other bodily fluid.

2. A solid test strip according to claim 1 wherein the electron mediator is a diaphorase enzyme.

3. A solid test strip according to claim 1 wherein the tetrazolium dye precursor is nitrobluetetrazolium ("NBT") or 2-(indophenyl)-3-(paranitrophenyl)-5-phenyl tetrazolium chloride ("INT").

4. A solid test strip designed for use in monitoring weight loss programs and capable of enabling a person to self-monitor weight loss on a daily basis in a sample of urine, saliva or other non-invasively obtainable bodily fluid, which provides a color signal indicative of the combined β-hydroxybutyrate and acetoacetate content of the sample upon being dipped in the sample, removed, allowed to rest briefly and read, which solid test strip comprises
1) an inert support layer and
2) a dried reagent layer comprising a porous material impregnated with
   a) β-HBD enzyme, which is either
      (i) obtained from Alcaligenes or another source such that it is uninhibited by chloride ions or
      (ii) is obtained from a source that is inhibited by chloride ions and is present in a concentration at least 10 to 20 times that used when the β-HBD is obtained from a source such that it is uninhibited by chloride ions,
   b) NAD
   c) a tetrazolium dye precursor
   d) an electron mediator capable of transferring an electron to said dye precursor to effect a color change and
   e) a sufficient quantity of a buffer having a pH of at least 7.0 but less than 8.5, to maintain the reaction pH below 8.5 but not less than about 7.0 when the strip is saturated with urine or other bodily fluid.

5. A solid test strip according to claim 4 wherein the electron mediator is a diaphorase enzyme.

6. A solid test strip according to claim 4 wherein the tetrazolium dye precursor is NBT or INT.

7. A solid test strip designed for use in monitoring weight loss programs and capable of enabling a person to self-monitor weight loss on a daily basis in a sample of urine, saliva or other non-invasively obtainable bodily fluid, which provides a color signal indicative of the combined β-hydroxybutyrate and acetoacetate content of the sample upon being dipped in the sample, removed, allowed to rest briefly and read, which solid test strip comprises
1) an inert support layer and
2) a dried reagent layer comprising a porous material impregnated with
   a) β-HBD enzyme, which is either
      (i) obtained from Alcaligenes or another source such that it is uninhibited by chloride ions or
      (ii) is obtained from a source that is inhibited by chloride ions and is present in a concentration at least 10 to 20 times that used when the β-HBD is obtained from a source such that it is uninhibited by chloride ions,
   b) NAD,
   c) a nitroprusside salt or a diazonuim salt in a quantity sufficient to react with both endogenous acetoacetate obtained by conversion thereto of β-hydroxybutyrate in the sample, and
   d) a sufficient quantity of a buffer have a pH about 8.5 or higher to maintain the strip at the same pH when saturated with sample.

8. A solid test strip according to claim 7 wherein the electron mediator is a diaphorase enzyme.

9. A solid test strip according to claim 7 wherein the tetrazolium dye precursor is NBT or INT.

10. A test strip according to claim 7 wherein ingredient (c) is sodium nitroprusside.

11. A test strip according to claim 7 wherein ingredient (c) is a diazonium salt.

12. A test strip according to claim 11 wherein ingredient (c) is 4-nitrobenzene-diazonium fluoborate.

13. A solid test strip designed for use in monitoring weight loss programs and capable of enabling a person to self-monitor weight loss on a daily basis in a sample of urine, saliva or other bodily fluid that is noninvasively obtainable, which provides a color signal, indicative of the total ketone bodies content of the sample upon being dipped in the sample, removed, allowed to rest briefly and read, which solid test strip comprises
1) an inert support layer and
2) a dried reagent layer comprising a porous material impregnated with
   a) β-HBD
   b) NAD
   c) a nitroprusside salt or a diazonium salt in sufficient quantity to
      (i) immediately react with the acetone present in the sample and stabilize it against volatilization and
      (ii) also react with the endogenous acetoacetate in the sample and with acetoacetate obtained by the conversion thereto of β-hydroxybutyrate in the sample and
   d) an electron mediator
   e) a sufficient quantity of a buffer having a pH of about 8.5 or higher to maintain the reaction pH at the same level when the strip is saturated with sample.

14. A solid test strip according to claim 13 wherein the electron mediator is a diaphorase enzyme.

15. A solid test strip according to claim 13 wherein the tetrazolium dye precursor is NBT or INT.

16. A test strip according to claim 13 wherein ingredient (c) is sodium nitroprusside.

17. A test strip according to claim 13 wherein ingredient (c) is a diazonium salt.

18. A test strip according to claim 16 wherein ingredient (c) is 4-nitrobenzene-diazonium fluoborate.

19. A method for monitoring the level of β-hydroxybutyrate present in a sample of urine or another human bodily fluid that can be noninvasively obtained, which comprises contacting said sample with a mixture comprising the following ingredients:
   a) β-HBD which either
      (i) has been obtained from Alcaligenes or another source such that it is not inhibited by chloride ions, or else
      (ii) has been obtained from a source such that it is inhibited by chloride ions and is present in an excess amount from 10 to 20 times the concentration utilized when the (β-HBD is not inhibited by chloride ions,
   b) NAD
   c) a tetrazolium dye precursor, d) an electron mediator and e) a buffer having a pH above 8.5 and measuring by electrochemical, spectrophotometric or fluoro metric means, or by comparison of the develop color to a preestablish color intensity standard, the amount of β-hydroxyrate in the sample.

20. A method according to claim 19 wherein the tetrazolium dye precursor is NBT or INT.

21. A method according to claim 19 wherein the electron mediator is a diaphoruse enzyme.

22. A method for monitoring the level of combined acetoacetate and β-hydroxybutyrate in a sample of human bodily fluid which comprises contacting the sample with a mixture of the following ingredients:

a) β-HBD b) NAD c) a tetrazolium dye precursor, d) an electron mediator, and e) a buffer having a pH that is over 7.0 but less than 8.5, and measuring by electrochemical, spectrophotometric or fluorometric means, or by comparison of the color developed to a preestablished color intensity standard, the combined amount of β-hydroxybutyrate and acetoacetate present in the sample.

23. A method according to claim 22 wherein the sample is urine or another fluid that can be noninvasively obtained and the β-HBD is either (I) obtained from Alcaligenes or another source such that it is not inhibited by chloride ions, (ii) or else has been obtained from a source such that it is inhibited by chloride ions and is present in an excess amount from about 10 to 20 times the amount utilized when the β-HBD is not inhibited by chloride ions.

24. A method according to claim 22 wherein the tetrazolium dye precursor is NBT or INT.

25. A method according to claim 22 wherein the electron mediator is a diaphorase enzyme.

26. A method for monitoring the level of combined acetoacetate and hydroxybutyrate in a sample of human bodily fluid which comprises contacting said sample with a mixture comprising the following ingredients:

a) β-HBD, b) NAD, c) a nitroprusside salt or a diazonium salt in a quantity sufficient to react with endogenous acetoacetate in the sample and acetoacetate obtained by conversion thereto of β-hydroxybutyrate in the sample, and d) a buffer having a pH of about 8.5 or higher and measuring by electrochemical, spectrophotometric or fluorometric means, or by comparison of the color developed to a preestablished color intensity standard, the amount of combined acetoacetate and β-hydroxybutyrate in the sample.

27. A method according to claim 26 wherein the sample is urine or another fluid that can be noninvasively obtained and the β-HBD is either (i) obtained from Alcaligenes or another source such that it is not inhibited by chloride ions, or else (ii) has been obtained from a source such that it is inhibited by chloride ions and is present in an excess amount from about 10 to 20 times the amount utilized when the β-HBD is not inhibited by chloride ions.

28. A method according to claim 26 wherein the tetrazolium dye precursor is NBT or INT.

29. A method according to claim 26 wherein the electron mediator is a diaphorase enzyme.

30. A method according to claim 26 wherein ingredient (c) is a nitroprusside salt.

31. A method according to claim 26 wherein ingredient (c) is a diazonium salt.

32. A method according to claim 31 wherein ingredient (c) is 4-nitrobenzene diazonium fluoborate.

33. A method for monitoring the level of total ketone bodies in a sample of human bodily fluid which comprises contacting said sample with a mixture comprising the following ingredients:

a) β-HBD, b) NAD, c) a nitroprusside or diazonium salt in an amount sufficient to
(i) react instantaneously with and stabilize acetone in the sample,
(ii) also react with endogenous acetoacetate in the sample and
(iii) also react with acetoacetate formed by conversion thereto of β-hydroxybutyrate in the sample, and d) a buffer having a pH of about 8.5 or higher, and measuring by electrochemical, spectrophotometric or fluorometric means, or by comparison of the color developed to a preestablished color intensity standard the amount of total ketone bodies in the sample.

34. A method according to claim 33 wherein the sample is urine or another fluid that can be noninvasively obtained and the β-HBD is either (i) obtained from Alcaligenes or another source such that it is not inhibited by chloride ions, or else (ii) has been obtained from a source such that it is inhibited by chloride ions and is present in an excess amount from about 10 to 20 times the amount utilized when the β-HBD is not inhibited by chloride ions.

35. A method according to claim 33 wherein the tetrazolium dye precursor is NBT or INT.

36. A method according to claim 33 wherein the electron mediator is a diaphorase enzyme.

37. A method according to claim 33 wherein ingredient (c) is a nitroprusside salt.

38. A method according to claim 33 wherein ingredient (c) is a diazonuim salt.

39. A method according to claim 38 wherein ingredient (c) is 4-nitrobenzene diazonium fluoborate.

* * * * *